US008320982B2

(12) United States Patent
LeBoeuf et al.

(10) Patent No.: US 8,320,982 B2
(45) Date of Patent: Nov. 27, 2012

(54) MULTI-WAVELENGTH OPTICAL DEVICES AND METHODS OF USING SAME

(75) Inventors: Steven Francis LeBoeuf, Raleigh, NC (US); Jesse Berkley Tucker, Knightdale, NC (US)

(73) Assignee: Valencell, Inc., Raleigh, NC (US)

( * ) Notice: Subject to any disclaimer, the term of this patent is extended or adjusted under 35 U.S.C. 154(b) by 615 days.

(21) Appl. No.: 12/519,011

(22) PCT Filed: Dec. 21, 2007

(86) PCT No.: PCT/US2007/026169
§ 371 (c)(1),
(2), (4) Date: Oct. 20, 2009

(87) PCT Pub. No.: WO2008/085411
PCT Pub. Date: Jul. 17, 2008

(65) Prior Publication Data
US 2010/0049017 A1 Feb. 25, 2010

Related U.S. Application Data (60) Provisional application No. 60/877,232, filed on Dec. 27, 2006.

(51) Int. Cl.
*A61B 5/00* (2006.01)
(52) U.S. Cl. ......................... 600/310; 600/323
(58) Field of Classification Search .................. 600/310, 600/312, 319, 322–323, 326, 316
See application file for complete search history.

(56) References Cited

U.S. PATENT DOCUMENTS

| | | | | |
|---|---|---|---|---|
| 5,673,692 A * | 10/1997 | Schulze et al. | ............... | 600/301 |
| 6,023,541 A * | 2/2000 | Merchant et al. | ............... | 385/20 |
| 6,070,093 A * | 5/2000 | Oosta et al. | ............... | 600/316 |
| 6,289,230 B1 * | 9/2001 | Chaiken et al. | ............... | 600/322 |
| 6,415,167 B1 * | 7/2002 | Blank et al. | ............... | 600/344 |
| 7,894,869 B2 * | 2/2011 | Hoarau | ............... | 600/344 |
| 8,059,924 B1 * | 11/2011 | Letant et al. | ............... | 385/12 |
| 2003/0222268 A1 | 12/2003 | Yocom et al. | | |
| 2005/0030540 A1 | 2/2005 | Thornton | | |
| 2006/0211924 A1 * | 9/2006 | Dalke et al. | ............... | 600/310 |
| 2009/0030350 A1 | 1/2009 | Yang et al. | | |

FOREIGN PATENT DOCUMENTS

| | | |
|---|---|---|
| EP | 1480278 A2 | 11/2004 |
| GB | 2408209 A | 5/2005 |
| WO | WO 00/24064 | 4/2000 |

OTHER PUBLICATIONS

FITRAINER, http://itami.com, downloaded/printed Feb. 2006.

* cited by examiner

*Primary Examiner* — Christopher Mahoney
(74) *Attorney, Agent, or Firm* — Myers Bigel Sibley & Sajovec, P.A.

(57) ABSTRACT

Multi-wavelength optical apparatus includes an optical emitter, and an energy transition layer positioned adjacent to the optical emitter. The energy transition layer generates multi-wavelength electromagnetic radiation when monochromatic light from the optical emitter passes therethrough. The energy transition layer includes a plurality of luminescent films, and each film is configured to luminesce at a respective different wavelength range when monochromatic light from the optical emitter passes therethrough. The plurality of luminescent films may be arranged in contacting face-to-face relationship or may be arranged in an array. The luminescent films may include rare-earth doped oxides, phosphors, metal-doped oxides, rare-earth doped nitrides, nanostructures, and/or nanostructured films, etc. The optical emitter may be a light emitting diode (LED), a laser diode (LD), an organic light-emitting diode (OLED), a resonant cavity light emitting diode (RCLED), and/or an edge-emitting diode (EELED).

23 Claims, 10 Drawing Sheets

MULTI-WAVELENGTH OPTICAL DEVICES AND METHODS OF USING SAME

RELATED APPLICATION

This application claims the benefit of and priority to U.S. Provisional Patent Application No. 60/877,232, filed Dec. 27, 2006, the disclosure of which is incorporated herein by reference as if set forth in its entirety.

FIELD OF THE INVENTION

The present invention relates generally to optical emitters and, more particularly, to multi-wavelength optical emitters.

BACKGROUND OF THE INVENTION

In multi-wavelength photoexcitation spectroscopy, independent control of multiple monochromatic excitation wavelengths is often required to characterize the wavelength-dependent optical properties in various media, such as semiconductors, biological chemicals, volatile organic vapors, ceramics, thin films, biological tissues, and the like. To classify as "monochromatic," the optical excitation wavelength must be spectrally narrow with respect to the spectral properties of the sample, providing high spectral resolution. Examples of such wavelength-dependent ("spectral") properties include optical absorption, fluorescence, transmission, reflection, polarization, and the like. Other high resolution spectral properties include the conversion of optical energy to other energies, such as with Raman spectroscopy, photoacoustic spectroscopy, photomagnetic spectroscopy, and the like. Because of the inhomogenities and/or size constraints that exist in many samples, a tight optical focus, often less than 100 μm in diameter, may be required to accurately assess the optical properties from background noise. In such case, all optical excitation wavelengths must focus at the same narrow point on a sample to provide accurate optical characterization.

To implement multi-wavelength photoexcitation spectroscopy, a variety of optical source-detector configurations can be employed. For example, a broadband optical source, such as a tungsten-halogen, mercury-arc, or xenon lamp, can be integrated into an optical spectrometer. In this case, the spectral width of the excitation beam can be controlled by manipulating the optical slit width and by implementing a high- or low-resolution optical diffraction grating. Unfortunately, this technique may be time consuming, as characterizing the optical properties of a given sample may be limited by the rotational speed of the optical diffraction grating. Furthermore, characterizing time-dependent optical properties may be compromised by the slow switching speed of the broadband sources. Lastly, being bulky, power-hungry, and delicate, this setup may be unsuitable for spectroscopy applications requiring user-portable, and perhaps wearable, spectrometry tools. Replacing the lamps with multiple lasers may eliminate problems associated with speed, as a diffraction grating is not needed, but adding lasers may compound problems associated with system cost and portability.

To increase portability and reduce cost, a single optical source, such as a laser diode (LD) can be configured as a controllable multi-wavelength emitter through a high-speed, electrically controllable Bragg reflector, via the electrooptic effect. By adjusting the voltage of the electrooptic electrodes, the peak excitation wavelength can be selected for spectroscopy applications. However, the spectral range of the peak wavelength, being limited by the maximum index of refraction differential, may be restricted to a few nanometers at best, and this may not be suitable for many spectroscopy applications. Broadening the spectral range can be achieved by introducing multiple laser diodes (LDs), light-emitting diodes (LEDs), or other compact optical point sources, but this may add complexity to a compact system. Namely, each additional wavelength range may not only require an additional optical emitter but also may require additional packaging and optical alignment. For example, in the case of LDs or LEDs, each optical wavelength range, from UV to visible to IR, may require a different semiconductor material system, each requiring its own packaging and optics. Moreover, each LED or LD may require optical alignment with respect to the other.

SUMMARY

In view of the above discussion, multi-wavelength optical emitters, with independent control of each wavelength on the same optical chip are provided. This is accomplished by integrating a monochromatic optical emitter point source with multiple light-transitioning films. In its most general form, the light-transitioning films convert light from the optical emitter into another form of energy, which may or may not be optical in nature. In some embodiments, the light-transitioning films are luminescent films, generating optical fluorescence in response to optical excitation from the optical emitter. In other embodiments, a light-emitting diode (LED) is divided into individually powered micro-mesas, each exciting fluorescence at a different wavelength in the different luminescent films. This is accomplished by aligning each luminescent film with an individual micro-mesa. Thus, the adjacent light transition light-emitting diode provides an ideal solution for low-cost, portable, real-time spectroscopy applications.

According to some embodiments of the present invention, low-cost, short-wavelength LEDs are combined with efficient luminescent films. For example, short wavelength visible LEDs (such as UV, blue, green, etc.) are integrated with luminescent films (such as rare-earth doped oxides, chlorides, fluorides, etc.) to generate multiple sharp optical emission bands. By selectively depositing specific luminescent films on individually controlled LED mesas fabricated on the same LED die, a multiwavelength LED can be generated with independent control of each luminescent wavelength. By fabricating micro-mesas, less than 100 μm in diameter, with selectively deposited luminescent films on the same LED die, a very compact point source for dozens of individually controlled optical wavelengths can be realized. This innovation can be applied not only to LEDs, but also to LDs, OLEDs (organic light-emitting diodes), and other optical point sources.

In its most basic form, this innovative approach relates to integrating an adjacent light transition layer within, about, or near a point source optical emitter, such that excitation light from the emitter is transformed into another form of energy, such as light (of a different wavelength/polarization), acoustic energy, thermal energy, mechanical energy, magnetic energy, electrical energy, chemical energy, nuclear energy, electromagnetic energy, and the like. When a light transition layer is integrated with an LED, the device is referred to as an "ALTLED" (adjacent light transition light-emitting diode). Here, the term "adjacent" refers to the fact that at least one point of the light transition film touches at least one point of the optical emitter (the excitation source). More specifically, embodiments of the present invention focus on adjacent luminescent films integrated with an LED (or the like) for an independently controlled multi-wavelength LED. In such case, the light transition is from a shorter optical wavelength to a longer optical wavelength, also known as optical down-conversion.

Because such a source can be very compact, portable, self-aligned, and low-cost, requiring low input power, an ALTLED, according to some embodiments of the present invention, can be directly applied to various noninvasive medical diagnostics applications. For example, an ALTLED can be integrated with a pulse oximeter for monitoring more health factors than simply blood oxygen levels. In such case, the ALTLED enables the real-time detection of bilirubin, blood urea nitrogen (BUN), electrolytes, hydration, carbon dioxide, and other blood and skin health factors through multi-wavelength excitation spectroscopy from the deep-UV to mid-IR. Conventional pulse oximetry, in contrast, typically employs only 2 wavelengths for gauging blood oxygen levels ($SpO_2$).

An ALTLED, according to some embodiments of the present invention, can also be applied towards biometric identification for monetary exchange and secured transactions. In this approach, multiwavelength spectroscopy can be used to characterize and verify unique spectral properties of the skin, hair, nails, or other externals on the human body. In many cases, 100% accuracy in personal identification is not needed but rather only enough accuracy to prevent the majority of fraudulent acquisitions. A low-cost, user-portable multiwavelength spectrometer would be ideal for such requirements.

Additionally, a variety of portable spectroscopy applications, such as pollution monitoring, mining exploration, and industrial controls, would benefit strongly from the ALTLED. In some cases, such as wearable health monitoring applications, an ALTLED may be the enabling technology needed to realize a new or emerging market altogether.

According to some embodiments of the present invention, a multi-wavelength optical apparatus includes an optical emitter that emits light along a light path, an energy transition layer positioned in the light path, and a detector configured to receive electromagnetic radiation generated by the energy transition layer. The apparatus is configured to receive an article between or adjacent to the energy transition layer and the detector such that the optical detector receives electromagnetic radiation generated by the energy transition layer that is reflected from and/or transmitted through the article. The energy transition layer generates multi-wavelength electromagnetic radiation when monochromatic light from the optical emitter passes therethrough. The energy transition layer includes a plurality of luminescent films, and each film is configured to luminesce at a respective different wavelength range when monochromatic light from the optical emitter passes therethrough. In some embodiments, the plurality of luminescent films are arranged in contacting face-to-face relationship.

In other embodiments, the plurality of luminescent films are arranged in an array. For example, the optical emitter may include an array of mesa structures and the plurality of luminescent films are arranged in a corresponding array, wherein each luminescent film is configured to luminesce at a respective different wavelength when monochromatic light from a respective mesa structure passes therethrough. The plurality of luminescent films may include rare-earth doped oxides, phosphors, metal-doped oxides, rare-earth doped nitrides, nanostructures, and/or nanostructured films, etc. The optical emitter may be a light emitting diode (LED), a laser diode (LD), an organic light-emitting diode (OLED), a resonant cavity light emitting diode (RCLED), and/or an edge-emitting diode (EELED).

According to other embodiments of the present invention, a method of noninvasively measuring a physiological property of a being includes illuminating a portion (e.g., finger, ear, earlobe, ear canal, tragus, meatus, concha, etc.) of a body of the being with multi-wavelength electromagnetic radiation generated by an energy transition layer, and detecting electromagnetic energy reflected from and/or transmitted through the body portion via a detector. The detected electromagnetic energy is indicative of the state of a physiological property of the being. For example, the detected electromagnetic energy may provide information about metabolic activity, blood properties, and/or tissue properties of the being. The energy transition layer generates multi-wavelength electromagnetic radiation when monochromatic light from an optical emitter passes therethrough.

In some embodiments, the energy transition layer includes a plurality of luminescent films, wherein each film is configured to luminesce at a respective different wavelength when monochromatic light from the optical emitter passes therethrough. In some embodiments, the plurality of luminescent films are arranged in contacting face-to-face relationship. In other embodiments, the plurality of luminescent films are arranged in an array. For example, the optical emitter may include an array of mesa structures and the plurality of luminescent films are arranged in a corresponding array, wherein each luminescent film is configured to luminesce at a respective different wavelength range when monochromatic light from a respective mesa structure passes therethrough. The plurality of luminescent films may include rare-earth doped oxides, phosphors, metal-doped oxides, rare-earth doped nitrides, nanostructures, and/or nanostructured films, etc. The optical emitter may be a light emitting diode (LED), a laser diode (LD), an organic light-emitting diode (OLED), a resonant cavity light emitting diode (RCLED), and/or an edge-emitting diode (EELED).

DETAILED DESCRIPTION

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of an organism. However, in some cases, the term "psychological" is called-out separately to emphasize aspects of physiology that are more closely tied to conscious or subconscious brain activity rather than the activity of other organs, tissues, or cells.

The term "body" refers to the body of a person (or animal) that may utilize an earpiece module according to embodiments of the present invention. Monitoring apparatus, according to embodiments of the present invention may be worn by humans and animals.

Figure 1:
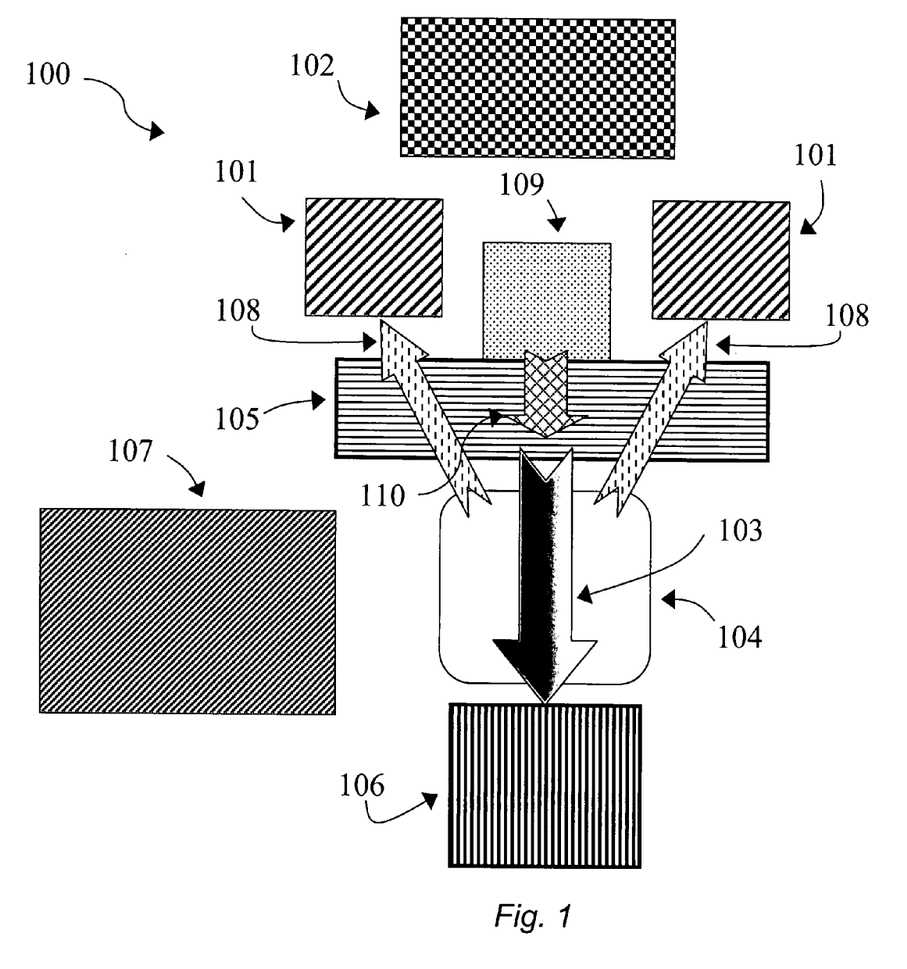
FIG. 1 illustrates a multi-wavelength optical source with detectors and analysis tools for spectroscopy, according to some embodiments of the present invention.

FIG. 1 illustrates a non-limiting embodiment of an innovative spectroscopy system 100, according to the present invention. The system 100 includes an electromagnetic source 109 adjacent to at least one energy transition layer 105, such that electromagnetic energy 110 from the source 109 is fully or partially converted/transitioned into energy 103. The converted energy 103 may pass through at least one sample under test 104 and the interaction between the energy 103 and the sample under test 104 may be measured by a detector 106. Similarly, some energy 108 may be reflected or altered in such a way that it does not pass entirely through the sample 104. The converted energy 103 is drawn with different shading from layers 105 to 104 to 106; this is to illustrate that the converted energy 103 is interacting with the sample under test 104, and the energy properties are changing throughout the interaction volume. This energy 108 or the absence thereof can be detected by detectors 101 located at or near the top of the sample 104. The electromagnetic source 109 can be powered by a power source 102, and information detected by the detectors 101 and 106 can be analyzed by an analyzer 107. The characteristic output of the analyzer 107 with respect to the converted energy 103 gives unique information about the sample under test 104.

In some embodiments of the illustrated system 100, the electromagnetic source 109 is a light-emitting diode (LED) or laser diode (LD) and the electromagnetic excitation energy 110 is in the optical wavelength range of ultraviolet (UV) through infrared (IR), for example, ranging from ~50 nm to 50 μm or, for example, from 200 nm to 10 μm. The energy transition layer 105 is preferably one or more luminescent films, generating converted optical energy 103 having one or more optical wavelengths differing from that of the optical excitation energy 110. In some embodiments, the luminescent film(s) 105 contains rare-earth elements for luminescence. For example, the film(s) 105 may include oxides, fluorides, chlorides, nitrides, sulfides, phosphates, arsenides, polymers, and the like doped with rare-earth elements or similar luminescent elements, molecules, or complexes. Under this configuration, the resulting multi-wavelength emitter is referred to as an "ALTLED" (adjacent light transition light-emitting diode) or "ALTLD" (adjacent light transition laser diode).

Not shown for reasons of clarity in FIG. 1 are potential interface layers between the source 109 and the transition layer 105, as well as energy guiding layers on the source 109 and the transition layer 105. These layers may be potentially integrated into one or more of the broad layers illustrated in FIG. 1. Namely, 109 represents the optical source as a whole, including the substrate, all epitaxial layer, contact layers, passivation layers, waveguiding layers, and the like. These fundamental layers are well known to those skilled in the art.

Figure 2:
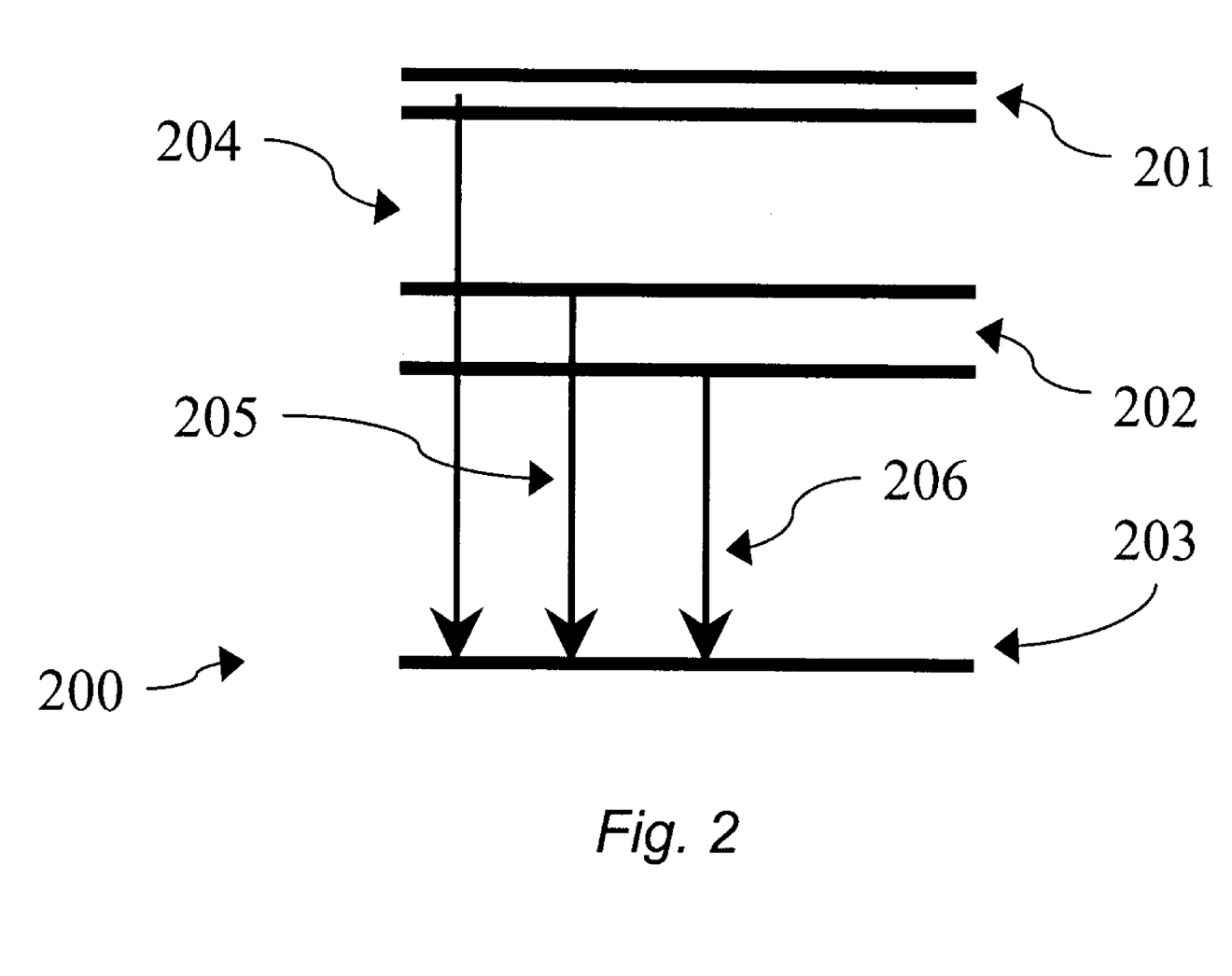
FIG. 2 illustrates the energy states in a luminescent film and depicts a method of time-dependent multi-wavelength spectroscopy that may be utilized in accordance with some embodiments of the present invention.

FIG. 2 illustrates the energy states and energy state transitions in an exemplary luminescent film. Here, the electron energy state 201 is more energetic than energy state 202, which is more energetic than energy state 203. In many cases, the energy states represent a collection of states that are energetically close to each other, such as the doublet states of 201 and 202. 204 represents a radiative recombination pathway for the energy state or combination of energy states 201. 205 and 206 represent higher and lower energy radiative recombination pathways for the doublet states of 202. The radiative transition 204 from 201 to 203 generates higher energy photons than the radiative transition 205 from 202 to 203, which generates higher energy photons than the radiative transition 206 from 202 to 203. Typically, the higher the energy separation between initial and final energy states, the faster the radiative recombination time. Thus, energy transition 204 is quicker than 205, and energy transition 205 is quicker than 206. Altogether, this provides an innovative method 200 of generating multiple time-dependent wavelengths using the same optical pulse 110 from an optical excitation source 109. Namely, a single pulse of optical energy 110 can excite multiple radiative transitions (such as 204, 205, and 206), each characterized by a particular wavelength 103 and radiative lifetime, and the time-dependent optical interactions in a sample under test 104 for each optical wavelength 103 can be differentiated by the wavelength and the radiative lifetime. More specifically, in a given sample under test 104, optical absorption at each wavelength 103 can be identified by the characteristic radiative lifetime of each wavelength 103—where each wavelength 103 is generated by the same optical excitation pulse 110.

Referring back to FIG. 1, in some embodiments of the present invention, the optical source 109 is a monochromatic LED or LD, and the energy transition layer 105 is preferably one or more luminescent films containing rare-earth elements. The characteristic time-dependent optical luminescence lifetime of each wavelength generated in the luminescent film or films 105 is used to differentiate the optical interactions of each wavelength within a sample under test 104. This way, multi-spectral characterization can be studied for each wavelength with a single monochromatic excitation source 109. An especial benefit of this technique is that only one photodetector 106, requiring no optical filters, is required to characterize each wavelength interaction because each wavelength interaction can be differentiated by the time-dependent response as opposed to the characteristic wavelength. Because optical filters are not needed for monitoring individual time-dependent responses, more optical energy is allowed to hit the photodetector 106, providing a higher overall sensitivity and simplicity of the spectrometer 100. Measuring multiple time-dependent responses in real-time can be achieved with serial and parallel electronic filtering of the signal. One limitation is that the monochromatic excitation source 109 must be pulsed with current pulses smaller than the radiative transition times for each radiative combination pathway (such as 204, 205, and 206). Multiple luminescent films 105 containing multiple luminescent particles, such as rare-earth dopants, can be deposited on the same structure, generating a multitude of luminescent wavelengths. As long as the radiative recombination times for these luminescent energy pathways do not overlap, the interaction of these wavelengths with a sample under test 104 can be monitored by one or more detectors (such as 101 and 106) and analyzers (such as 107).

Figure 3:
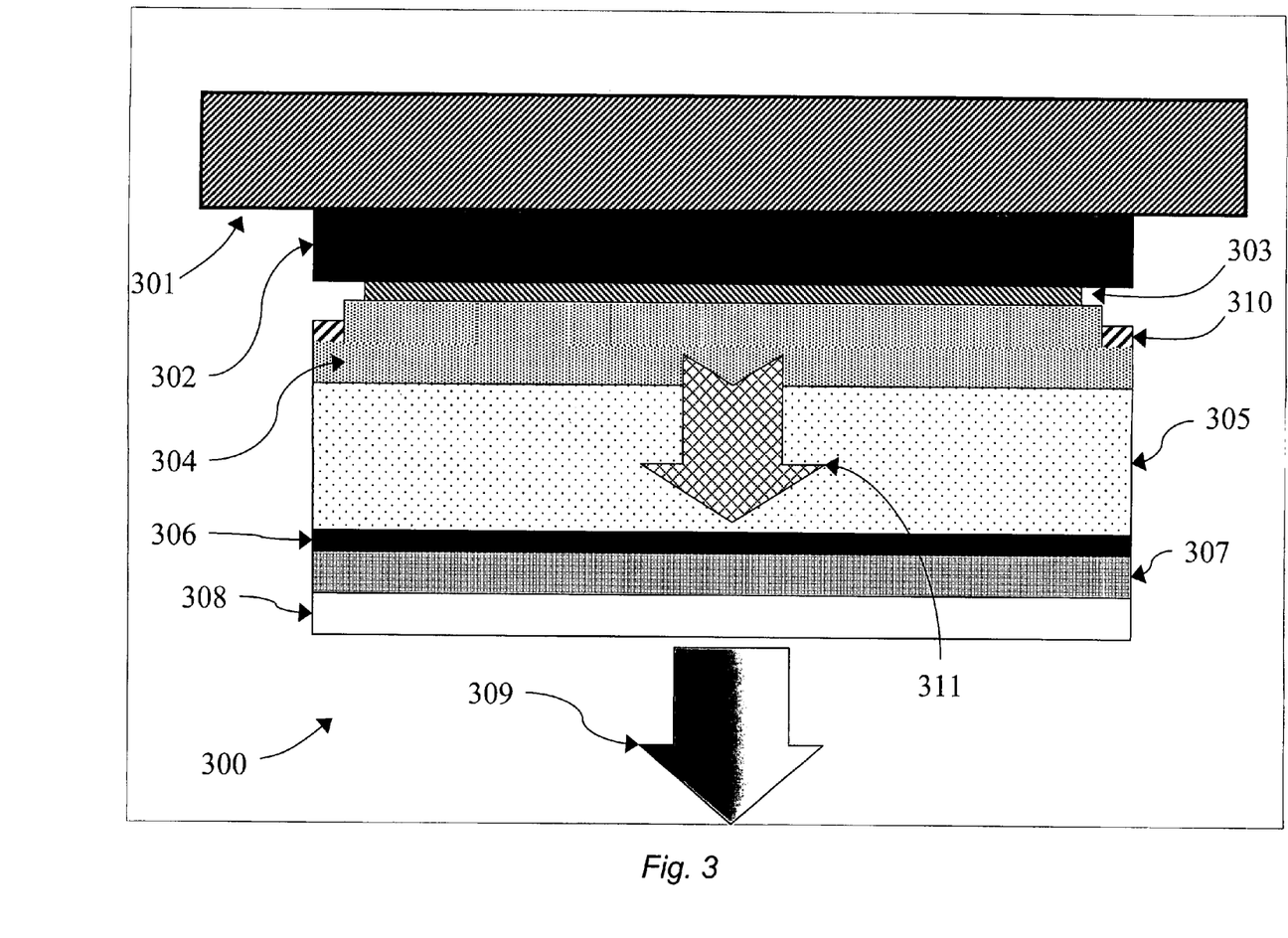
FIG. 3 illustrates an ALTLED with adjacent, vertically stacked luminescent films, according to some embodiments of the present invention.

FIG. 3 depicts an embodiment of an ALTLED 300 combining the optical source 109 and luminescent film(s) 105 of FIG. 1. In this design the optical source 109 may contain a thermal packaging layer 301 and a die submount 302 for mounting an LED or LD die. The LED or LD die is composed of an active layer 304, p- and n-metal contact layers 303 and 310, and a substrate layer 305. The LED can be a variety of different styles, such as an organic light emitting diode (OLED), a resonant cavity light emitting diode (RCLED), and edge-emitting diode (EELED), and the like. The active layer 304 contains various p- and n-doped layers and light generating layers ("active regions") composed primarily of semiconductor or polymer material and various dopants. In many cases, the active layer 304 can include a semiconductor heterostructure, to provide high confinement of electron-hole pairs for more efficient radiative recombination. Also included in the active layer 304 are passivation and reflection layers, typically at the surface of the semiconductor or polymer material. Passivation is typically achieved by the deposition of an oxide or dielectric film at the surface of the semiconductor or polymer, and reflection layers are typically achieved by the deposition of a reflective metal at the surface of the semiconductor, polymer, or passivation layer. The substrate layer may be a variety of crystalline or partially crystalline layers. Preferably, the substrate layer is an optically transparent crystalline substrate. For example, sapphire makes an excellent transparent crystalline substrate for aluminum indium gallium nitride (AlInGaN) LED epitaxy. The substrate layer 305 must be substantially optically transparent to the excitation light 311 to be suitable for the ALTLED 300. The luminescent film(s) 105, adjacent to the substrate layer 305, may be composed of an interface layer 306, a light-emitting layer 307, and a light guiding layer 308. The purpose of the interface layer 306 is to support adhesion and optical coupling between the substrate layer and the light-emitting layer 307. For example, the interface layer may facilitate optical transmission of excitation light 311 into the light-emitting layer 307 and may guide luminescence 309 away from the substrate 305 and towards the guiding layer 308. The light-guiding layer 308 facilitates optical extraction from the light-emitting layer. The luminescence 309 is illustrated with graded horizontal shading to indicate more than one optical wavelength can exist in the same beam 309. In some embodiments, the light-emitting layer also serves as the interface layer and/or the light guiding layer. 306, 307, and 308 can be fabricated from dielectric films. For example, the interface layer 306 and the light-guiding layer 308 can be resonant optical structures composed of alternating dielectric layers of dissimilar refractive index, such as Bragg reflectors or resonant transmission structures. The light-emitting layer 307 is typically a dielectric layer or polymer doped with rare-earth elements or rare-earth complexes or compounds.

A non-limiting exemplary process for producing the ALTLED 300 of FIG. 3 is described herein. AlInGaN LED epitaxy is grown on the epi-ready frontside of a crystalline, optically transparent c-plane sapphire substrate via commercialized metal-organic chemical vapor deposition (MOCVD). The total LED film thickness usually ranges from 2 to 4 µm to minimize strain in the epitaxy, but thicker films are often preferred. For AlInGaN, n-type layers are usually grown first, followed by the active region (for generating light) and p-type layers. Thus, 303 is usually a p-contact and 310 is usually an n-contact. Following MOCVD epitaxial growth, the LED wafer is introduced into a pulsed laser deposition (PLD) tool, for depositing the rare-earth doped luminescent films on the epi-free backside of the sapphire wafer. Magnetron sputtering of the luminescent films, as opposed to PLD, is also acceptable; other deposition techniques are also suitable. During PLD, the frontside of the LED wafer can be protected by facing the frontside away from the PLD growth zone or by covering the frontside with a protective "sacrificial oxide," such as $SiO_2$, to be subsequently removed. PLD targets can be generated by sintering powdered mixtures of oxides, such as gallium oxide or aluminum oxide, with rare-earth oxides, such as $Eu_2O_3$. During PLD, these targets are ablated by an excimer laser under high vacuum (~$5 \times 10^{-8}$ torr), and the by-products settle on the substrate to form a contiguous, crystalline oxide film. Film growth can be performed at a wide range of temperatures, but ~700-900° C. is preferred. It is important to maintain a temperature that will not destroy the AlInGaN epitaxy on the front side of the wafer. Multiple luminescent films can be deposited sequentially by changing the PLD target inside the PLD deposition tool; this can be automated during PLD growth without having to open the PLD reactor or break vacuum. For example, a europium-doped gallium oxide target can be ablated first, followed by a neodymium-doped gallium oxide target, then followed by a praseodymium-doped target, etc., yielding a layered luminescent film of the same order structure as the ablated target procession.

It should be noted that growth conditions during PLD, magnetron sputtering, MOCVD, and the like, play an important role in the optical quality of the deposited films. For example, growth at higher temperatures typically encourages high-crystalline growth and supports dopant incorporation at optically active lattice sites. Furthermore, by nanoscale engineering, nanostructures can form quantum dots or "quantum wells" which further support radiative recombination efficiency brighter optical output. For example, depositing thin, nanoscale (<100 nm) films of lower band gap material surrounded by higher band gap material can result in higher radiative recombination efficiency within the lower band gap film. The film deposition process described herein, and methods of incorporating high-brightness nanostructures, are a non-limiting examples.

Following growth, the resulting wafer can be processed as a standard AlInGaN LED, using photolithography steps well known to those skilled in the art. However, the luminescent oxide films on the backside should be protected throughout processing. Processing typically starts with a solvent clean of the wafer surface, sometimes followed by an acid clean. The luminescent rare-earth-doped oxide films on the sapphire backside can be protected by utilizing a sacrificial layer of protective photoresist during acid cleans and oxide etching steps. Following the clean, selective p-contacts are formed on the surface of the AlInGaN epitaxy, followed in order by mesa formation, n-contact formation, surface passivation, and bond pad formation. Typical p-contact metallizations are nickel oxide-gold alloy (NiO/Au), nickel, platinum, or silver. Typical n-contact metallizations are Ti/Al, Al, or Ti alloys. Metallization can be formed via standard e-beam or sputtering techniques. Mesa formation is typically executed by dry-etching approaches, with chlorine-based chemistries, such as reactive ion etching (RIE) and inductively coupled plasma etching (ICP etching). The mesas are formed to aid with light extraction and to define regions for the n-contact layer. The etched regions typically serve as the n-contact interface whereas the mesa tops serve as the p-contact interface, for the n- and p-contact metallization respectively. Most typically, the p-contact layers are metallized first, before mesa formation, to protect the delicate p-type epitaxy from detrimental RIE or ICP etching steps. Surface passivation is typically executed by the sputtering or plasma-enhanced chemical vapor deposition (PECVD) of silicon dioxide or silicon nitride, though other dielectrics are also possible. Ti/Ni/Au bond pads are then patterned by selectively etching holes in the passivation layer along the n- and p-metal contact regions. These bond pads serve as the location for wirebonds during subsequent LED packaging.

The fabricated LED wafer is then diced or sawed to generate hundreds to thousands of LED die, typically 1 $mm^2$ in area. These die are then flip-chip bonded to a silicon submount, and the submount is mounted to thermal packaging (for heat extraction). In some cases, the submount is not necessary and the LED die is attached directly to the thermal packaging, with the AlInGaN epitaxy facing down (towards the thermal packaging) and the luminescent film facing up (for light extraction). As with the LED fabrication process, ALTLED sawing, dicing, and packaging can be executed with standard recipes well known to those skilled in the art. Of special importance is that care must be taken to protect the luminescent films on the backside of the wafer. This can be done by applying a protective tape over the luminescent films to prevent scratching or other mechanical damage during sawing, dicing, packaging, and other back-end processes. The device process described herein is a non-limiting example.

Figure 4:
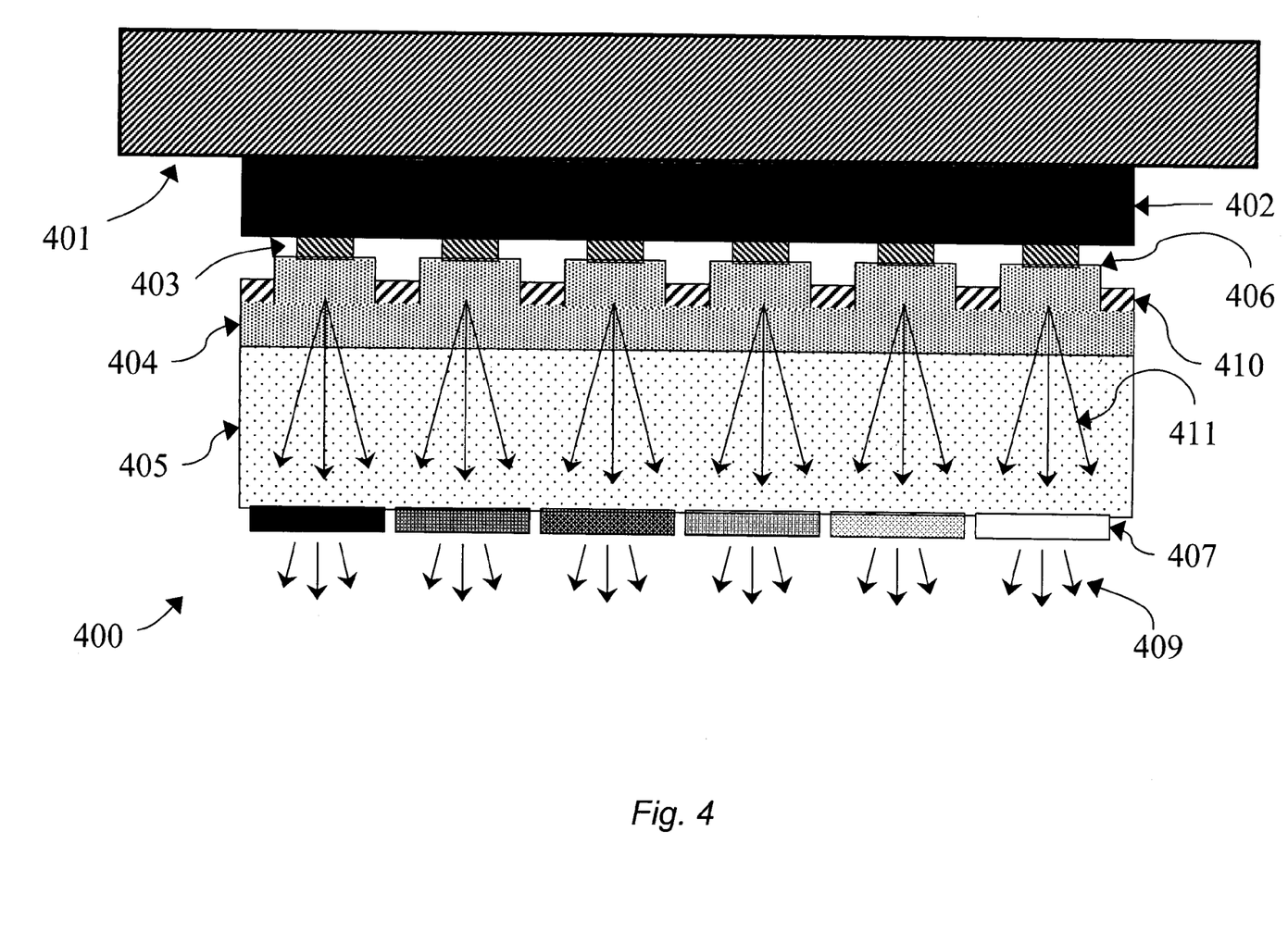
FIG. 4 illustrates an ALTLED with adjacent, horizontally arrayed luminescent films paired with individually powered mesas, according to some embodiments of the present invention.

FIG. 4 depicts an ALTLED 400, according to some embodiments of the present invention, with individually controlled mesas. In this design the optical source 109 may contain a thermal packaging layer 401 and a die submount 402 for an LED or LD die. The LED or LD die is composed of an active layer 404, p- and n-metal contact layers 403 and 410, and a substrate layer 405. The LED or LD can be a variety of different styles, such as an OLED, an RCLED, and the like. The active layer 404, can be identical to layer 304 of FIG. 3, and the substrate layer 405 can be identical to layer 305 of FIG. 3. However, the shape of the active layer 404 contains multiple mesa structures 406 along the surface of the active layers 404. (As with FIG. 3, the passivation and reflection layers at the surface of the mesa are not shown for simplicity.) Excitation light 411 from each mesa 406 is coupled with a particular luminescent film from the luminescent film array 407 on the substrate backside. Note that for the purpose of clarity, each individual film of film array 407 is indicated in FIG. 4 by a separate layer with differing shading. Each film of the luminescent film array 407 can be a combination of 306, 307, and 308 of FIG. 3. The key difference is that the luminescent films of array 407 are divided into individual films emitting at individual luminescent wavelengths. These individual films may be connected or spaced apart, and they are differentiated primarily by their characteristic luminescence wavelength(s). In a preferred embodiment, these individual films are all made of the same basic oxide film (such as gallium oxide, aluminum oxide, magnesium oxide, and the like), but each film contains one or more rare-earth dopants that are different from that of neighboring films, thereby generating different luminescent wavelengths from different films. It should be noted that in many cases each individual film of the film array 407 emits luminescent energy at more than one optical wavelength. For example, one mesa element of the mesa array 406 may excite one film of the film array 407 generating multiple luminescent wavelengths 409 from the film.

The production of ALTLED 400 can be similar to that of ALTLED 300, with two notable exceptions. Firstly, because several micro-scale mesas are patterned along the surface of the AlInGaN epitaxy, the etch conditions for ICP mesa etching are preferably performed at lower RF power to prevent mesa damage. Namely, the mesa etching rate of ALTLED 400 should be substantially slower than that of ALTLED 300. For example, ALTLED 400 may require a mesa etch rate of one-half that of ALTLED 300. Secondly, while depositing luminescent films on the substrate backside, shadow masks are used to selectively deposit each luminescent film having a different rare-earth dopant. This can be accomplished by indexing a shadow mask in-situ during growth by a distance of ~50 to 100 µm or more for each deposited film. This stands in contrast with ALTLED 300 of FIG. 3, where multiple luminescent films, each having a different rare-earth dopant or combination of rare earth dopants, are deposited sequentially and uniformly across the entire substrate backside.

Figure 9:
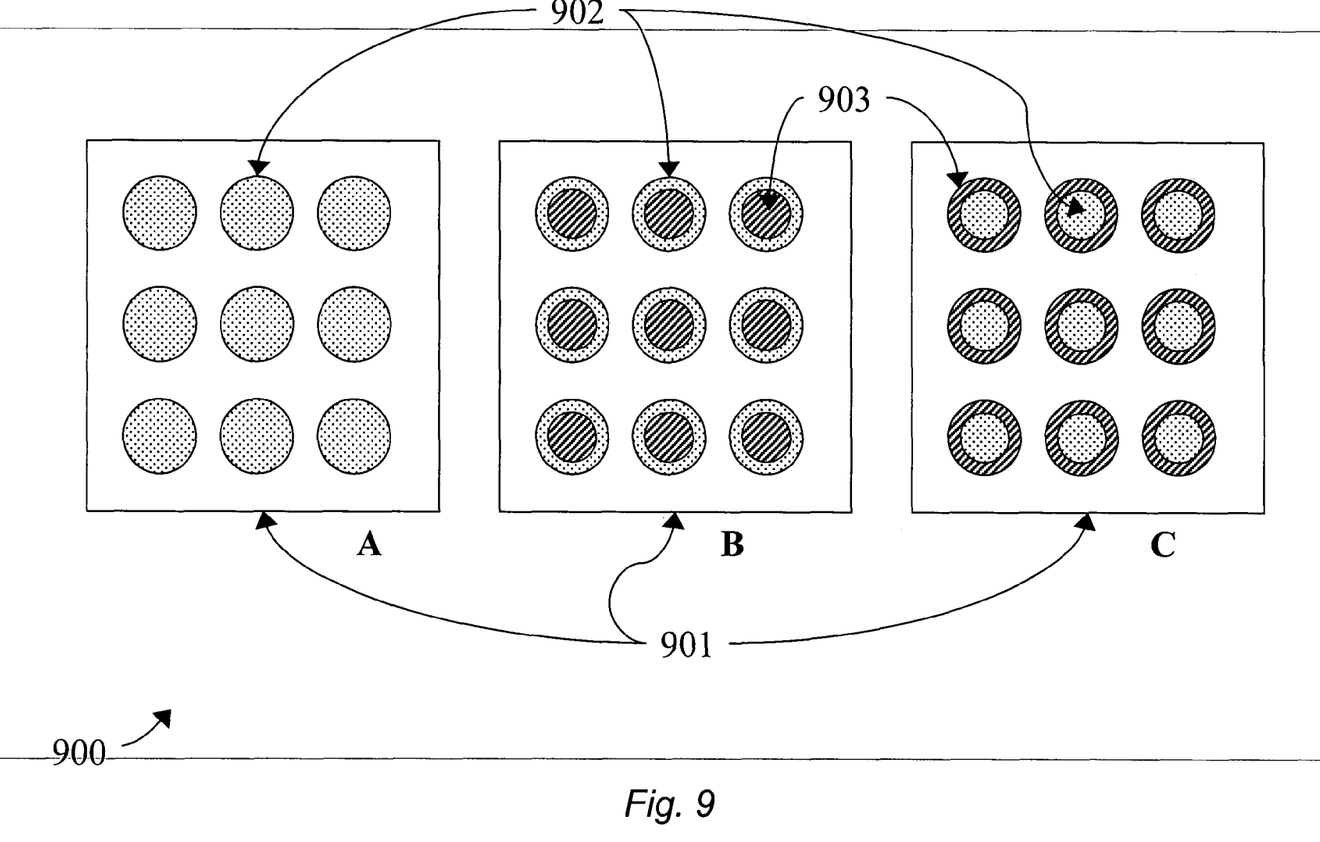
FIG. 9 is a top plan view of mesa-pumped luminescent films that may be utilized in accordance with some embodiments of the present invention.

FIG. 9 shows a top-level depiction of how mesas 902 might be designed and arrayed for the ALTLED of FIG. 4. It should be noted that FIG. 9 is a simplified top-level drawing for the top surface of an ALTLED; the passivation layers, reflection layers, and packaging are not shown for simplicity. Essentially, the mesas 902 can take any geometry or array configuration achievable by photolithographic principles, but a few exemplary embodiments are shown in FIG. 9. In each case, the mesas are spaced apart by roughly half the length of the diameter of the mesa, though this distance is quite flexible. The emphasis is that light 411 from each mesa 902 should excite primarily one of the films 407 on the substrate 405 backside, and this excitation light 411 should not significantly excite neighboring films. Thus, the mesas 902 should be spaced apart far enough to prevent optical interaction between neighboring mesas and neighboring films. In A, the film 407 corresponding to each mesa 902 is aligned directly below, or nearly directly below, each mesa 902. In B and C, the films 903, rather than being below the mesas 902 are adjacent to each mesa. In B, each mesa 902 is shaped like a doughnut, with a void at the center of active layer 404 material, and each luminescent film 903 is located in the center of this doughnut. In C, the situation is reversed from B, and the luminescent film 903 is shaped like a doughnut, with a void at the center of the film 903, and each mesa 902 is located in the center of this doughnut. In FIG. 9, layer 903 can be the same film or films as that of layer 407. During fabrication of these mesas 902, via RIE or ICP etching, edge-shaping must be considered to reduce scattering and encourage light extraction towards the bottom (substrate side) of the optical emitter. Similarly, sidewall smoothing and passivation may be necessary not only for enhanced optical extraction but also electrical passivation. In the AlInGaN system, smoothing can be achieved by post-ICP wet etching in KOH solutions; passivation can be achieved by high temperature anneals in gaseous ambient, and the like. These fundamental techniques are understood by those skilled in the art. It should also be noted that in some cases, the mesas 902 and luminescent films 903 are designed to emit light from the tops or sides as opposed to the bottoms of the overall device.

Figure 5:
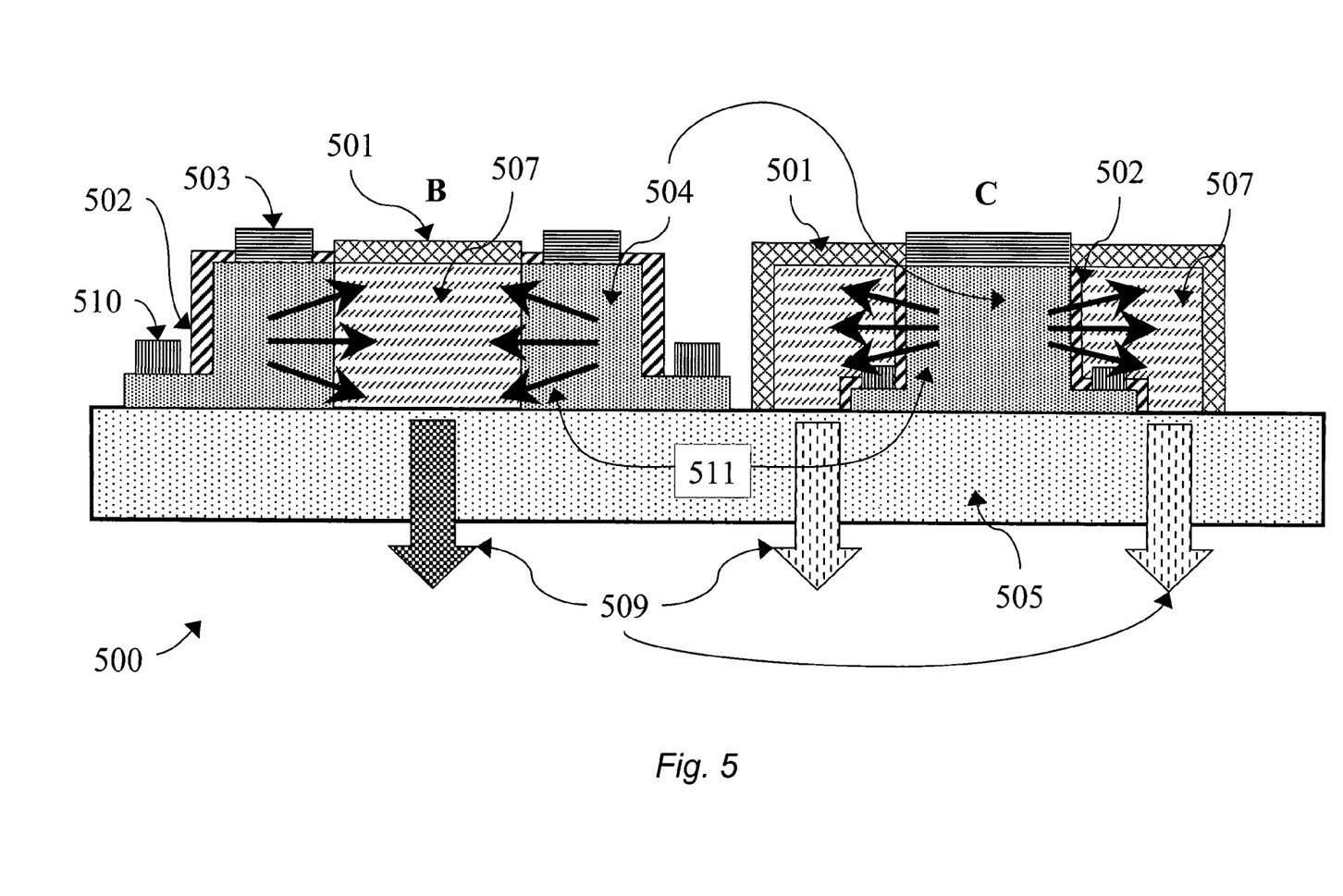
FIG. 5 is a side-view of mesa-pumped luminescent films that may be utilized in accordance with some embodiments of the present invention.

FIG. 5 shows side-views 500 of B and C in FIG. 9, respectively. As indicated by the layer shading, B and C have the same basic layers, but the geometries are different. P- and n-contact layers 503 (403) and 510 (410) supply current to the active layer 504 (404). The energy transition layer, or more specifically the luminescent film, 507 can be located on the inside of the active layer doughnut 504 (as in B) or the outside of the active layer doughnut 504 (as in C). The active layer 504 may contain a passivation layer, as described previously, and a guiding layer 502 may help direct light 511 generated in the active layer 504 to the film 507 for optical excitation. This guiding layer 502 can be a reflector, a dielectric stack, a Bragg reflector, or the like. Adjacent to the film 507 is a reflective layer 501 for directing emission energy 509, such as fluorescent light, towards the transparent substrate 511 and out of the ALTLED. In some cases, this reflective layer 501 can be replaced with a guiding layer for directing light out the top (away from the substrate 505) of the device rather than towards the bottom (towards the substrate 505). The reflective layer may be a metal, but dielectric reflectors, such as resonant cavities and Bragg reflectors, are also suitable.

Figure 6:
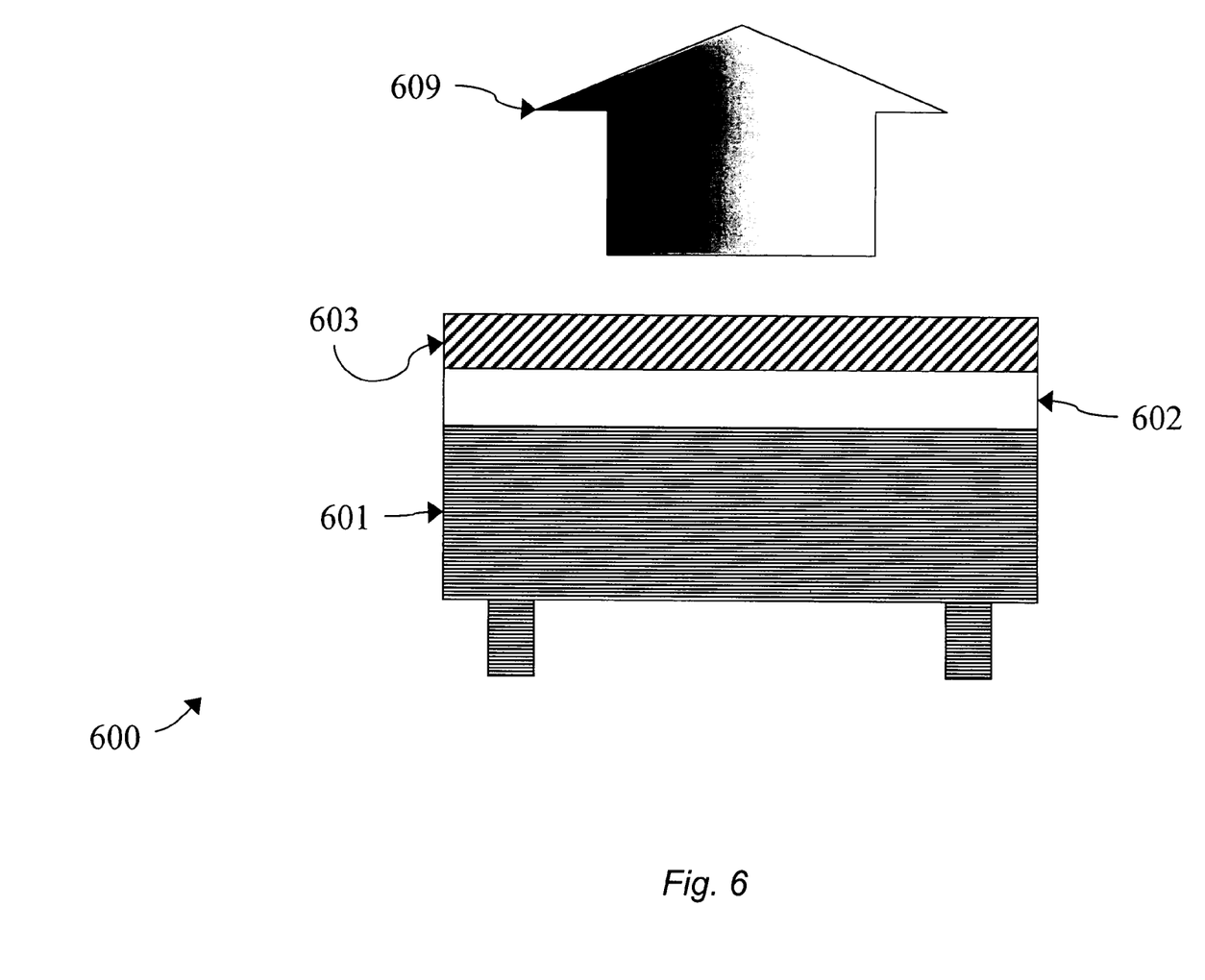
FIG. 6 illustrates an ALTLED having an LED and luminescent film packaged together, according to some embodiments of the present invention.

FIG. 6 illustrates an ALTLED (or ALTLD) 600, according to some embodiments of the present invention, where the optical emitter 109 is configured as a packaged optical emitter 601 with a transparent window layer 602 coated with an energy transition layer 603. The energy transition layer 603 converts light from the packaged emitter 601 to another form of energy 609. Preferably, the energy transition layer 603 is an optical film and the energy 609 is luminescence from the excitation of rare-earth dopants in the optical film. The optical emitter package is preferably a TO-5 package, Bergquist package, or the like. The package may be thermally conductive and may have connectors for supplying electrical power to the optical emitter. The optical emitter is an LED or and LD, such that 601 is a packaged LED or LD. In one embodiment, the energy transition layer 603 is a collection of films for generating various optical wavelengths upon excitation from the packaged optical emitter 603. In one embodiment of a packaged ALTLED 600, an ALTLED or ALTLD, such as 300 or 400, is integrated into a packaged optical emitter 601, such that neither layer 602 nor 603 is required for generating and guiding multiple optical wavelengths. This is because these layers are, in effect, already incorporated in layer 407 or within the combination of layers 306, 307, and 308. However, a protective light guiding window 602 may still be integrated to protect ALTLED components.

Figure 7:
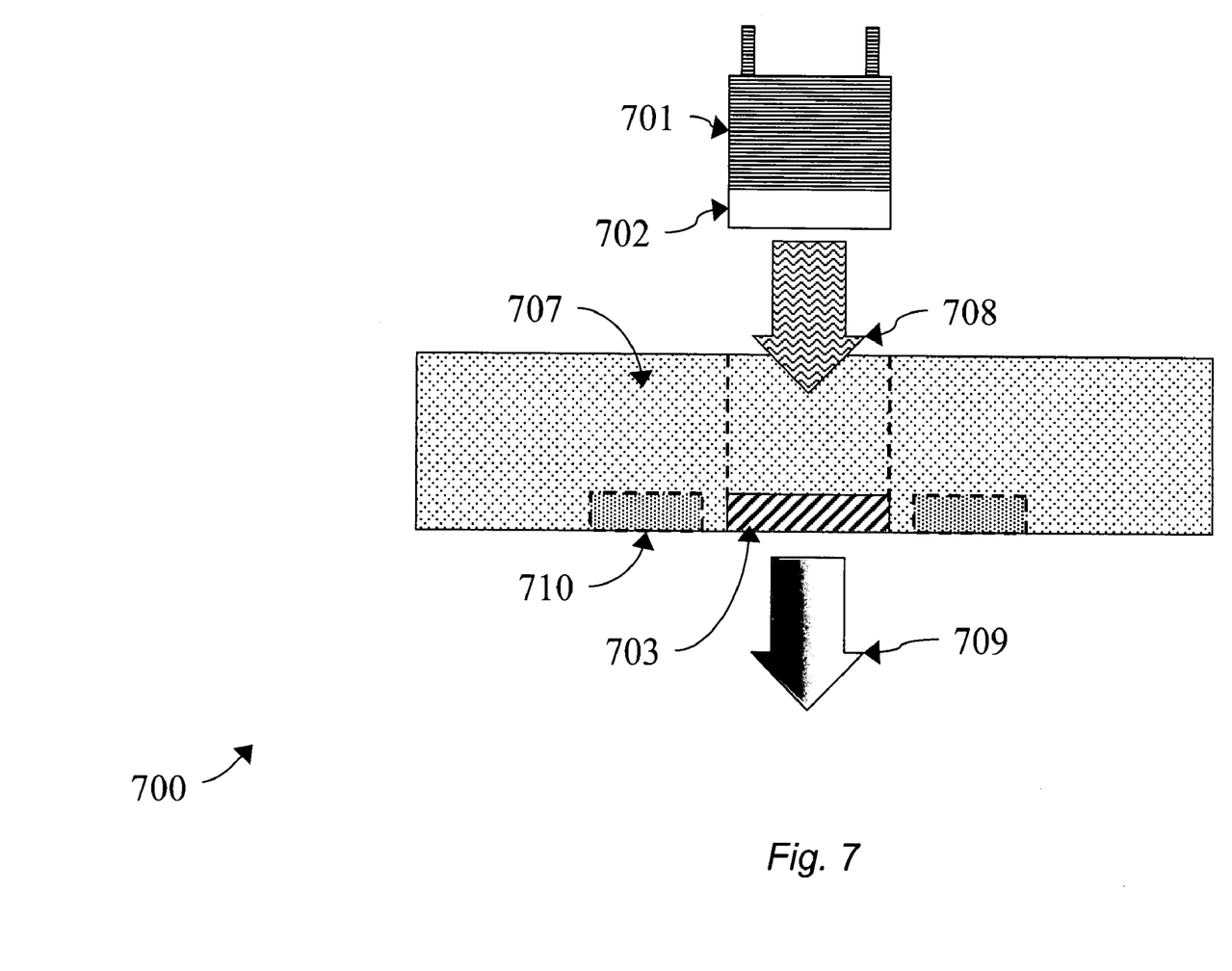
FIG. 7 illustrates a packaged ALTLED, according to some embodiments of the present invention, and wherein the LED package and the film package are bifurcated and assembled together.

In the ALTLED (or ALTLD) 700 of FIG. 7, the packaged LED 701 and optical window 702 can be bifurcated from the energy transition layer 703 such that 703 is part of a separate package. The packaged LED 701 fits snuggly inside a hole or space (denoted by the dashed vertical lines) built into the secondary package 707. The LED 701 is shown in exploded view outside of the secondary package 707 for clarity. The secondary package 707 may also contain sensor fixtures 710 for mounting photodetectors such as photodiodes, photoconductors, photomultiplier tubes, and the like, and the package may be composed of virtually any solid material, preferably thermally conducting material, such as metals, ceramics, thermally conductive polymers, and the like. When assembled together, the ALTLED 700 operates the same way as ALTLED 600. Excitation light 708 from the LED (or LD) stimulates luminescence 709 in the energy transition layer 703 for spectroscopy applications. The layer materials and films used in ALTLED 700 are identical or similar to that of ALTLED 600.

Figure 8:
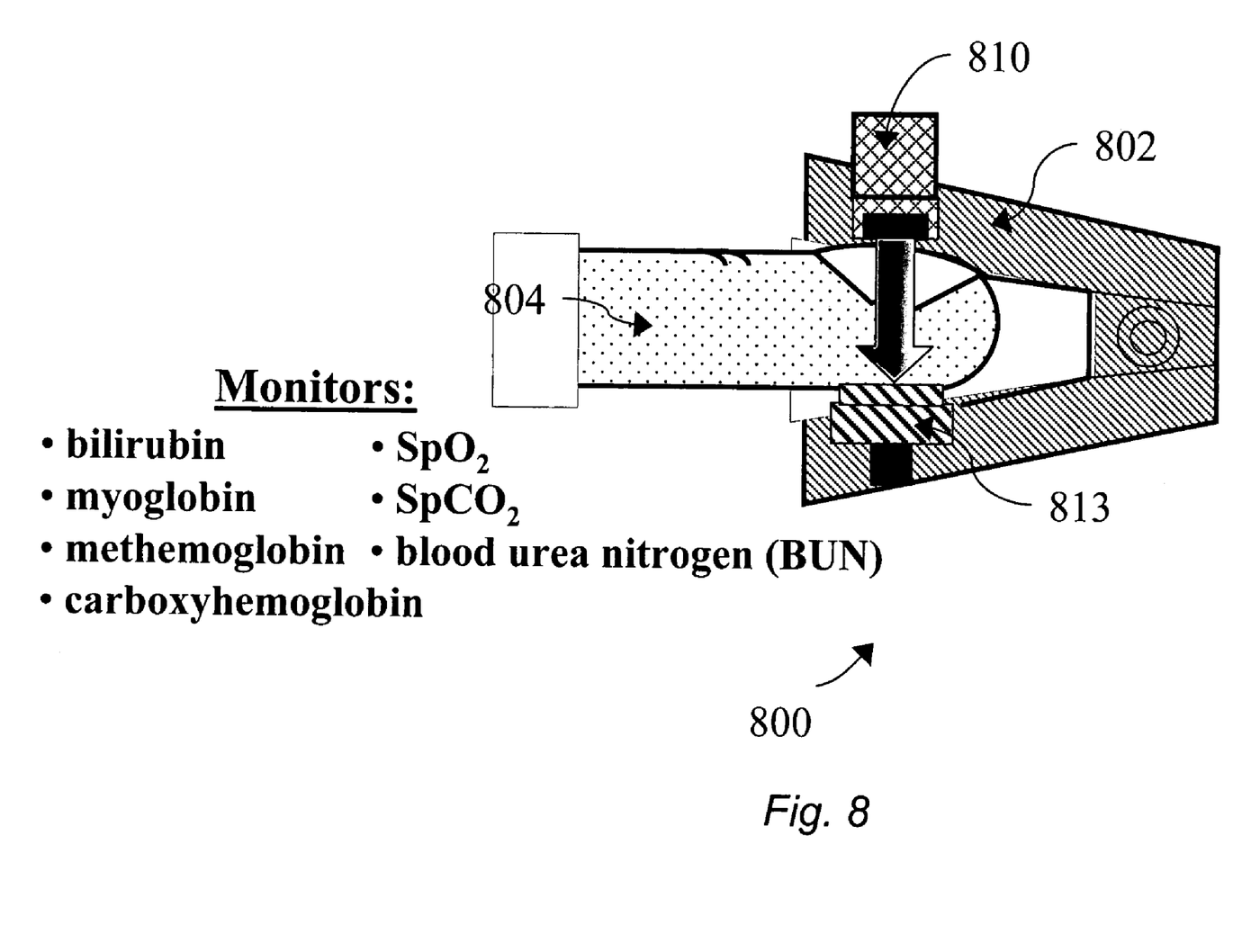
FIG. 8 illustrates an ALTLED integrated into a pulse oximeter, according to some embodiments of the present invention.
Figure 10:
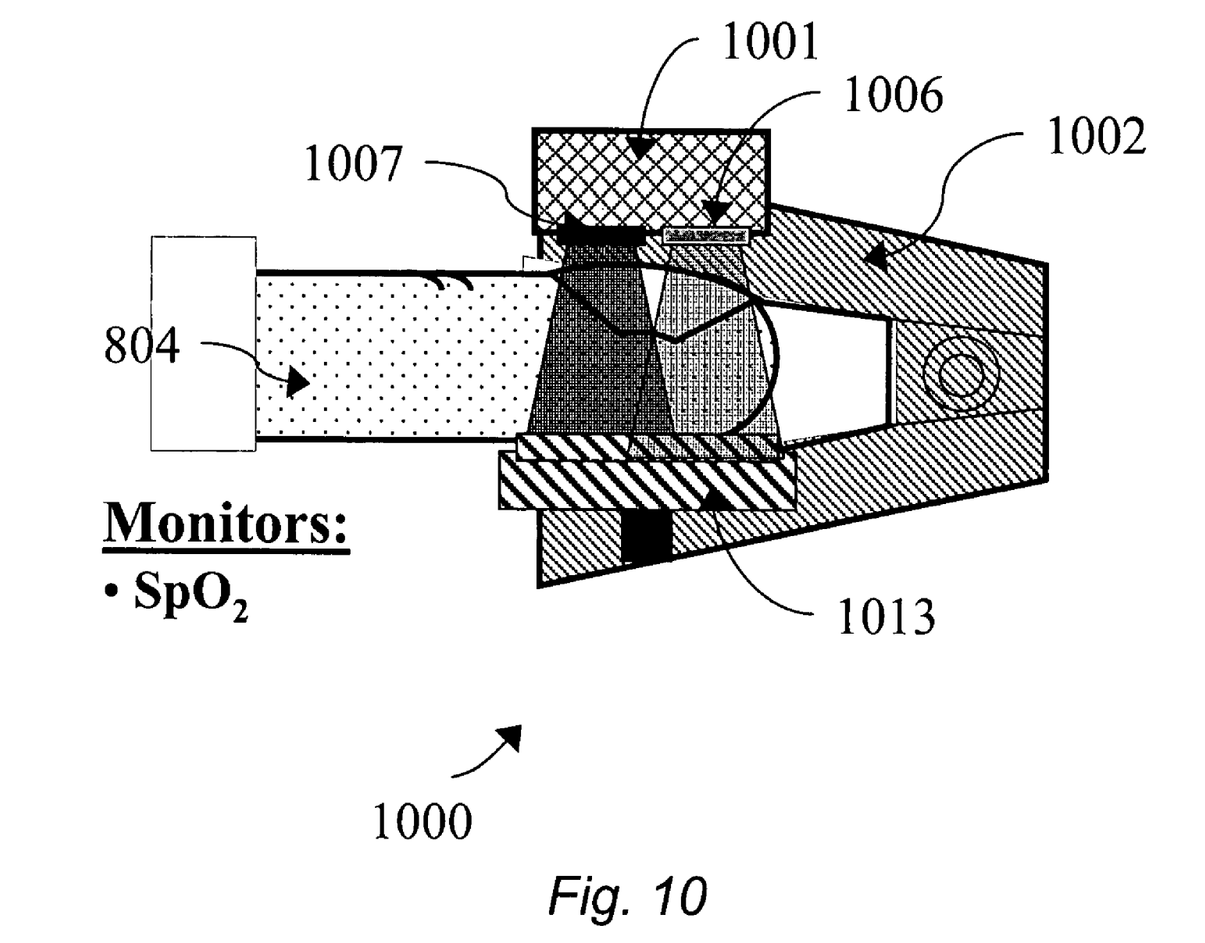
FIG. 10 illustrates an LED integrated into a conventional pulse oximeter.

FIG. 8 and FIG. 10 compare an ALTLED pulse oximeter 800, according to embodiments of the present invention, with a conventional pulse oximeter 1000. Pulse oximetry is a standard noninvasive technique of estimating blood gas levels. Pulse oximeters typically employ 2 separate LEDs 1006 and 1007 packaged in a mounting piece 1001, with one LED emitting red light and the other emitting near-IR light; an optical detector 1013 (typically a photodiode) is positioned on a finger clip 1002 for estimating the ratio of oxygenated to deoxygenated blood in the finger 804 based on color changes in the blood. The earlobe and other regions can be used in place of the finger 804 as long as an artery or vein is in the optical path. In general, the optical wavelengths pass through arteries or veins, and these optical wavelengths are selectively absorbed by various blood metabolites, typically blood gas carriers such as hemoglobin. These metabolites can change color in response to the incorporation or removal of various blood gases, such as oxygen, carbon dioxide, carbon monoxide, and other inhaled gases. Though only 2 optical wavelengths are generated in the conventional optical LEDs 1006 and 1007, embodiments of the present invention provide additional wavelengths to replace or enhance the conventional wavelengths. For example, by replacing the standard LED sources 1006 and 1007 with a single packaged multiwavelength ALTLED or ALTLD 810, many different optical wavelengths can be generated from the same compact optical emitter, eliminating the need for multiple LEDs 1006 and 1007. This enables novel multiwavelength spectroscopy in the same pulse oximetry paradigm. Namely, by adding additional visible and infrared wavelengths, myoglobin, methemoglobin, carboxyhemoglobin, bilirubin, $SpCO_2$, and blood urea nitrogen (BUN), and the like can be estimated and/or monitored in real-time, in addition to the conventional pulse oximetry $SpO_2$ measurement. The optical source can include light-emitting diodes (LEDs), laser diodes (LDs), or other compact optical sources. In some cases, optical energies from the optical sources can be guided with waveguides, such as fiber optics. The optical detector 813 can include photodiodes (PDs), avalanche photodiodes (APDs), photomultipliers, or other compact optical detectors. The optical detector 813 can include optical filters. Similarly, the optical detector 813, as with the general case of detector 106, can be an array of filtered photodetectors, such as filtered photodiodes. Because only one LED is needed for the novel ALTLED pulse oximeter 800, the surface area of emitted light is much less than that of multiple LEDs 1006 and 1007, allowing a much smaller photodetector 813 to be incorporated as opposed to the larger photodetector 1013. This reduces dark noise and enhances sensitivity of the ALTLED pulse oximeter 800 as compared with its conventional counterpart 1000.

The ALTLED pulse oximetry approach 800 of FIG. 8, replacing multiple LEDs with a single monolithic multiwavelength LED, has several advantages over packaging several individual LEDs in a pulse oximetry package:

1. Wavelength flexibility is afforded for the same mesa array, by choice of rare-earth-doped films on the sapphire backside; many optical wavelengths can fit in the same 1 mm$^2$ die, allowing complete analysis of one small point along the human body, such as the "filet mignon" region of the ear lobe and the tip of the finger.
2. Adding additional wavelengths does not increase pulse oximeter size, maintaining high portability while dramatically increasing functionality; this is especially important for paramedics, point-of-use, and home healthcare markets, where low-profile monitoring is preferred.
3. Packaging and optical alignment is incredibly simplified, as only one LED needs to be packaged (as opposed to several different LEDs from 4 different semiconductor materials). This simplifies the die attach process, the wire bonding process, the optical alignment process, and the packaging design required for thermal matching.
4. Because each mesa is identical, each optical wavelength can be driven with the same current driver; additionally, temperature- and age-related LED changes will be roughly identical for all wavelengths.
5. Because the mesas (~100 μm diameter) are so small in comparison with standard LEDs (~600×600 μm$^2$), a greater optical power density can be generated via the same drive current, reducing the required photodiode size, lowering dark noise, and thereby increasing the overall optical sensitivity of the system.

An ALTLED or ALTLD, according to embodiments of the present invention, can be implemented in a variety of spectroscopy applications, such as physiological analysis, biometric analysis, pollution monitoring, water quality monitoring, and the like. Pulse oximetry has been outlined simply as an exemplary embodiment. It should be understood by those skilled in the art that this invention covers a broad range of spectroscopy applications which may or may not be medical in nature.

It should be reemphasized that the spectroscopy system 100 of FIG. 1 need not be limited to optical spectroscopy. As discussed earlier, the energy transition film 105 is meant generally to convert one form of energy to another. As a specific example, the optical emitter 109 may generate optical wavelengths 110 that stimulate photoacoustic resonance in 105, generating sonic energy. This photoacoustic film 105 can be a standard carbon-based photoacoustic film or a novel film such as a semiconductor or polymer with internal polarization. For this novel film, optical excitation energy 110 can be used to screen dipoles in the film, thereby causing a physical displacement in the film through the piezoelectric effect. More specifically, by shining light at a thin AlInGaN heterostructure near the absorption edge of one or more quantum wells, the polarization dipoles can be screened by optically excited electron-hole pairs, resulting in a displacement in the thin AlInGaN heterostructure. If the optical energy is pulsed at acoustic frequencies, or harmonics thereof, the displaced film will generate acoustic energy 103. Similarly, the energy transition film can be a photomagnetic film, generating magnetic energy 103 upon optical excitation 110. Various other energy transition films 105 can be employed for the novel spectroscopy system 100. Many such energy transitioning films are well known by those skilled in the art.

Though FIG. 10 shows the novel application of an ALTLED to transmission-mode pulse oximetry, it should be understood that the embodiments of the present invention also apply to reflection-mode pulse oximetry, as well as combinational approaches. In such case, the photodetector element 1013 may be in the same plane as the ALTLED to better capture reflected light 108.

According to other embodiments of the present invention, transdermal drug delivery devices which emit an emitted optical signal through the skin and/or one or more blood vessels, and detect an optical signal relevant to the drug molecule concentration delivered to a patient are provided. The emitted wavelength or wavelengths of light used are dependent on several factors, including the optical absorption properties of the skin, the optical absorption or fluorescence properties of the drug molecule, and the available range of optical detection devices. The detected wavelength range of interest can be the primary optical signal given off by the optical emitter, or a secondary wavelength such as a fluorescent emission.

According to other embodiments of the present invention, measurement of a reflected optical absorption over a wavelength range to determine the concentration of a drug molecule delivered to a patient can be obtained. This may involve a continuous wavelength range or a measurement of several distinct wavelengths, or a measurement at a single wavelength.

Other embodiments of the present invention relate to the measurement of the optical fluorescence of a drug molecule to determine the concentration of the drug molecule delivered to a patient. This may involve optical excitement of the drug molecule at a continuous wavelength range or several distinct wavelengths, or at a single wavelength. The determination of the drug molecule concentration delivered to the patient may be inferred from an optical emission detected over a continuous wavelength range or at several distinct wavelengths, or at a single wavelength.

Other embodiments of the present invention relate to the use of a fluorophore delivered in tandem with a drug molecule. The fluorophore concentration delivered to the patient is measured optically, and the concentration of the drug molecule delivered to the patient can be inferred.

Other embodiments of the present invention relate to the use of a measurement of the optical properties of a known constant optical property to provide a reference for the optical measurements of a drug molecule or fluorophore concentration. This reference optical property is a common attribute that changes little from patient to patient. This reference optical property is used to more effectively gage the concentration of drug molecules delivered to the patient based on the optical properties of the reference and the optical properties of the drug molecule or fluorophore.

Other embodiments of the present invention relate to the use of a feedback loop in which the optical measurement of the drug molecule concentration delivered to the patient is used to control the active transdermal drug delivery mechanism.

Other embodiments of the present invention relate to the use of a transdermal dosimeter device during the transdermal drug delivery device design phase to reduce the costs of repeated blood sampling and in-vitro blood testing.

This may also reduce the pain inflicted on clinical trial participants. This may involve measuring drug molecule concentrations in either blood samples, solvent samples, or direct transdermal measurement.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A multi-wavelength optical apparatus that is positionable adjacent to a body of a being, comprising:
   an optical emitter that emits light along a light path;
   an energy transition layer positioned in the light path, wherein the energy transition layer comprises a plurality of luminescent films, and wherein at least two of the films are configured to luminesce at different time-dependent optical luminescence lifetimes when light passes therethrough; and
   an optical detector that receives electromagnetic radiation generated by the interaction between luminescent energy from the energy transition layer and a region of the body.

2. The apparatus of claim 1, wherein the detector is a pulse oximeter detector configured to detect a ratio of oxygenated to deoxygenated blood in a body of a subject.

3. The apparatus of claim 2, wherein the apparatus is configured to receive a finger of a subject between the energy transition layer and the detector.

4. The apparatus of claim 2, wherein the apparatus is configured to receive an earlobe, ear canal, tragus, antitragus, meatus and/or concha of a subject between the energy transition layer and the detector.

5. The apparatus of claim 1, wherein the apparatus comprises a transdermal drug delivery device, wherein the optical emitter emits light through the skin of a subject, and wherein the detector is configured to detect an optical signal passing through or reflecting from the skin and/or at least one blood vessel that is relevant to a drug molecule concentration delivered to the subject.

6. The apparatus of claim 1, wherein the detector is a spectroscopic detector configured to detect biometric identification data.

7. The apparatus of claim 1, wherein the plurality of luminescent films are arranged in contacting face-to-face relationship.

8. The apparatus of claim 1, wherein the optical emitter comprises an array of mesas that generate the light and the apparatus generates an optical power density that is directly proportional to the number of mesas.

9. The apparatus of claim 1, wherein the plurality of luminescent films comprise rare-earth doped oxides, phosphors, metal-doped oxides, rare-earth doped nitrides, nanostructures, and/or nanostructured films.

10. The apparatus of claim 1, wherein the optical emitter comprises a light emitting diode (LED), a laser diode (LD), an organic light-emitting diode (OLED), a resonant cavity light emitting diode (RCLED), and/or an edge-emitting diode (EE-LED).

11. A method of noninvasively measuring a physiological property of a being, comprising:
    illuminating a portion of a body of the being with multi-wavelength electromagnetic radiation generated by an energy transition layer, wherein the energy transition layer comprises a plurality of luminescent films, wherein at least two of the films are configured to luminesce at different time-dependent optical luminescence lifetimes when light from an optical emitter passes therethrough; and
    detecting electromagnetic energy reflected from and/or transmitted through the body portion via a detector, wherein the detected electromagnetic energy is indicative of the state of a physiological property of the being.

12. The method of claim 11, wherein the detector is a pulse oximeter detector configured to detect a ratio of oxygenated to deoxygenated blood in a body of a subject.

13. The method of claim 11, wherein the body portion comprises a finger.

14. The method of claim 11, wherein the body portion comprises a portion of an ear.

15. The method of claim 11, wherein the physiological property includes metabolic activity, blood properties, and/or tissue properties.

16. The method of claim 11, further comprising delivering a dosage of a drug transdermally to the being prior to the illuminating step, and wherein the detecting step comprises detecting an optical signal passing through the skin or at least one blood vessel of the being that is relevant to a drug molecule concentration delivered to the being.

17. The method of claim 11, wherein the plurality of luminescent films are arranged in contacting face-to-face relationship.

18. The method of claim 11, wherein the plurality of luminescent films are arranged in an array.

19. The method of claim 11, wherein the plurality of luminescent films comprise rare-earth doped oxides, phosphors, metal-doped oxides, rare-earth doped nitrides, nanostructures, and/or nanostructured films.

20. The method of claim 11, wherein the optical emitter comprises a light emitting diode (LED), a laser diode (LD), an organic light-emitting diode (OLED), a resonant cavity light emitting diode (RCLED), and/or an edge-emitting diode (EE-LED).

21. A multi-wavelength optical apparatus, comprising:
an optical emitter that emits light along a light path;
an energy transition layer positioned in the light path, wherein the energy transition layer comprises a plurality of luminescent nanostructured films, and wherein each nanostructured film is configured to luminesce at a respective different wavelength range and at a respective different time corresponding to a different time-dependent optical luminescence lifetime when monochromatic light from the optical emitter passes therethrough; and
a detector configured to receive electromagnetic radiation;
wherein the apparatus is configured to receive an article adjacent to the energy transition layer and the detector, and wherein the optical detector is configured to receive electromagnetic radiation generated by the energy transition layer that is reflected from and/or transmitted through the article.

22. A method of noninvasively measuring a physiological property of a being, comprising:
illuminating a portion of a body of the being with multi-wavelength electromagnetic radiation generated by an energy transition layer, wherein the energy transition layer comprises a plurality of luminescent nanostructured films, and wherein each nanostructured film is configured to luminesce at a respective different wavelength and at a respective different time corresponding to a different time-dependent optical luminescence lifetime when monochromatic light from the optical emitter passes therethrough; and
detecting electromagnetic energy reflected from and/or transmitted through the body portion via a detector, wherein the detected electromagnetic energy is indicative of the state of a physiological property of the being.

23. A method of noninvasively measuring a physiological property of a being, comprising:
illuminating a portion of a body of the being with multi-wavelength electromagnetic radiation generated by an energy transition layer, wherein the energy transition layer generates multi-wavelength electromagnetic radiation at different times corresponding to respective different time-dependent optical luminescence lifetimes of the energy transition layer when monochromatic light from an optical emitter passes therethrough; and
detecting electromagnetic energy reflected from and/or transmitted through the body portion via a detector, wherein the detected electromagnetic energy can be differentiated by time-dependent responses and is indicative of the state of a physiological property of the being.

* * * * *